US008645074B2

(12) United States Patent
Parida

(10) Patent No.: US 8,645,074 B2
(45) Date of Patent: Feb. 4, 2014

(54) METHOD FOR RECONSTRUCTING EVOLUTIONARY DATA

(75) Inventor: Laxmi P. Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 1252 days.

(21) Appl. No.: 11/942,022

(22) Filed: Nov. 19, 2007

(65) Prior Publication Data

US 2009/0132584 A1     May 21, 2009

(51) Int. Cl.
    *G06F 19/00*      (2011.01)
    *G06F 19/14*      (2011.01)
    *G06F 19/10*      (2011.01)
    *G06F 17/10*      (2006.01)
    *G06F 7/58*      (2006.01)

(52) U.S. Cl.
USPC .................................. 702/19; 703/2; 703/11

(58) Field of Classification Search
None
See application file for complete search history.

(56) References Cited

U.S. PATENT DOCUMENTS

2005/0216208 A1 *   9/2005   Saito et al. ...................... 702/20
2005/0277135 A1 *   12/2005   Zabeau et al. ..................... 435/6

OTHER PUBLICATIONS

Minichiello et al. (The American Journal of Human Genetics (2006) vol. 79, pp. 910-922; published online on Sep. 27, 2006).*
Wiuf et al. (Genetics (2000) vol. 155; pp. 451-462).*
Wu, Y. et al. "Improved Algorithms for Inferring the Minimum Mosaic of a Set of Recombinants." Journal of Bioinformatics and Computational Biology, vol. 5(2(a)):181-200 2007.
Gusfield, D. et al "A Decomposition Theory for Phylogenetic Networks and Incompatible Characters" Journal of Computational Biology, vol. 14(10): 1247-1272, 2007.

* cited by examiner

*Primary Examiner* — Lori A Clow
(74) *Attorney, Agent, or Firm* — Ryan, Mason & Lewis, LLP

(57) ABSTRACT

Techniques for reconstructing evolutionary data of a set of genomic data are provided. The techniques include obtaining a set of genomic data, determining a chronological order of one or more mutations within the set of genomic data, determining a chronological order of one or more recombinations within the set of genomic data, determining a position of each recombination within the set of genomic data, and combining the chronological order of the one or more mutations, the chronological order of the one or more recombinations and the position of each recombination to reconstruct evolutionary data of the set of genomic data.

16 Claims, 10 Drawing Sheets

FIG. 3

| GROUP 0 | C1, C10, C80, C4, C85, C20, C32, C86 AND C110 | 302 |
|---|---|---|
| GROUP 1 | C100, C121, C7, C51, C12, C39 AND C117 | |
| GROUP 2 | C11, C48, C137, C27, C108 AND C50 | |
| GROUP 3 | C52, C9, C53, C5, C45, C123 ABD C103 | |
| GROUP 4 | C38, C107, C114, C54, C140 AND C115 | |
| GROUP 5 | C6, C3, C120 AND C93 | |
| GROUP 6 | C33, C2 AND C92 | |
| GROUP 7 | C74, C34, C29 AND C150 | |
| GROUP 8 | C40 AND C81 | |
| GROUP 9 | C47, C16, C91 AND C8 | |
| GROUP 10 | C143 | |
| GROUP 11 | C21 | |
| GROUP 12 | C36 | |
| GROUP 13 | C19 | |
| GROUP 14 | C24 | |
| GROUP 15 | C148 | |
| GROUP 16 | C118 | |

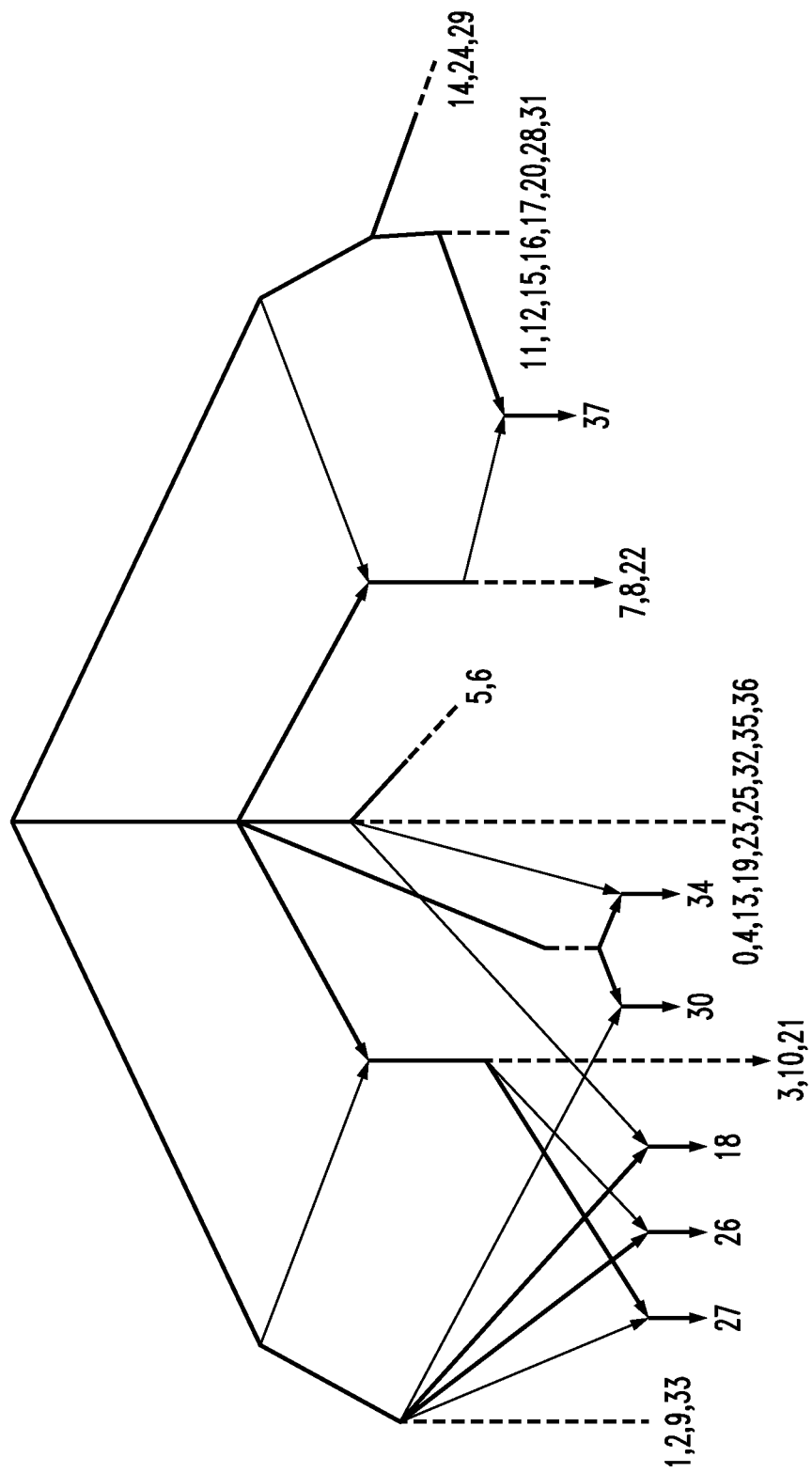

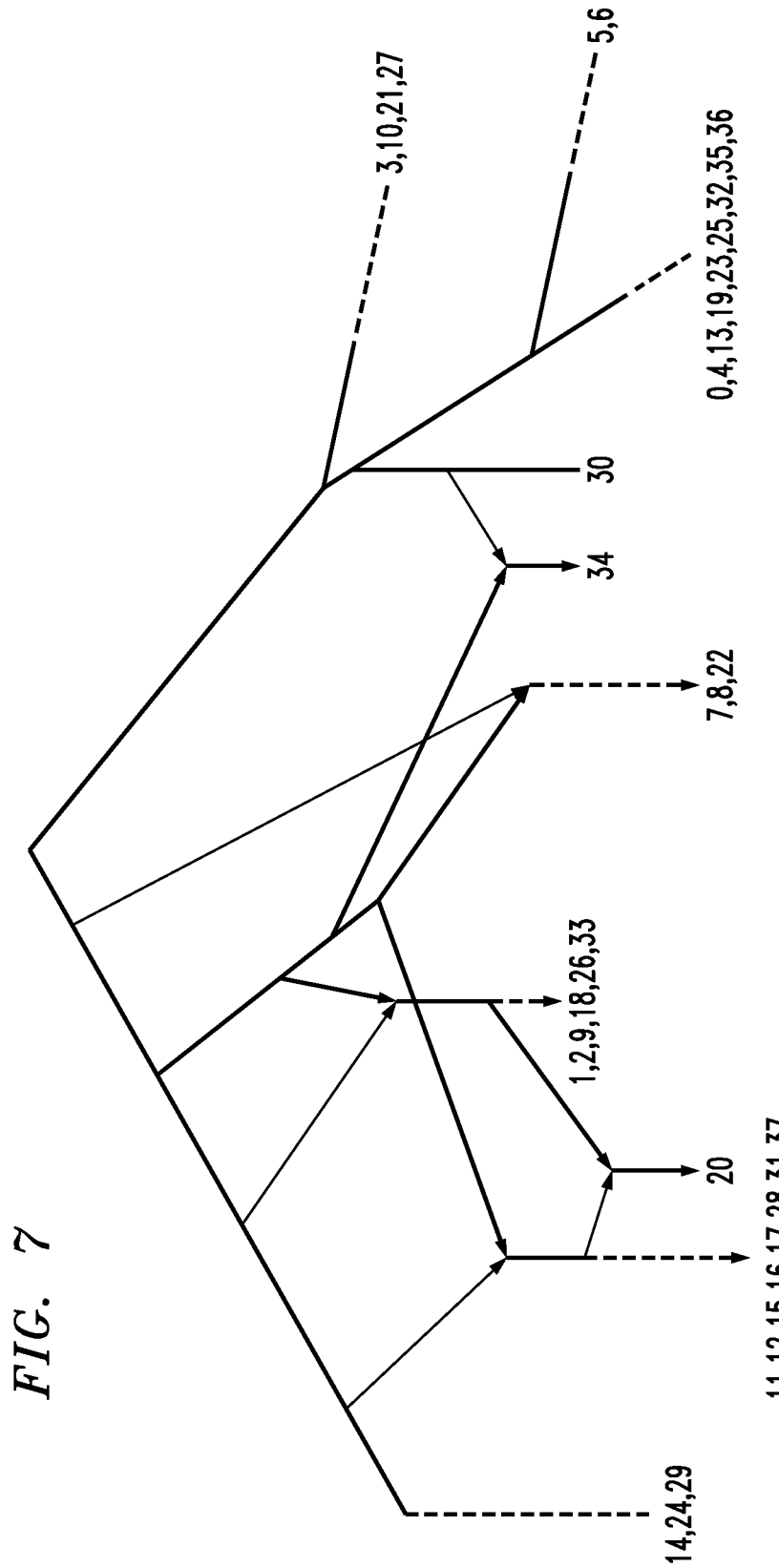

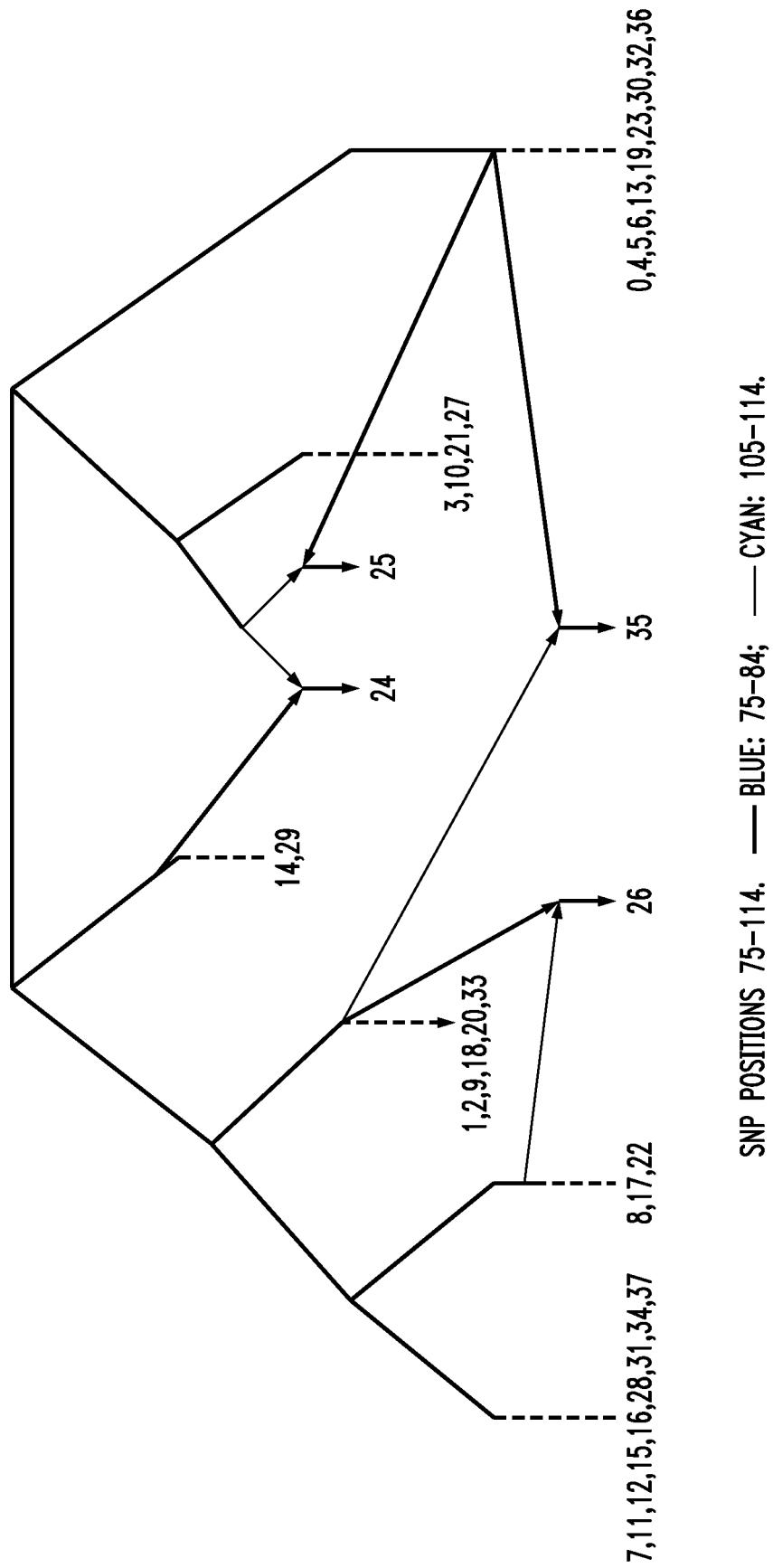

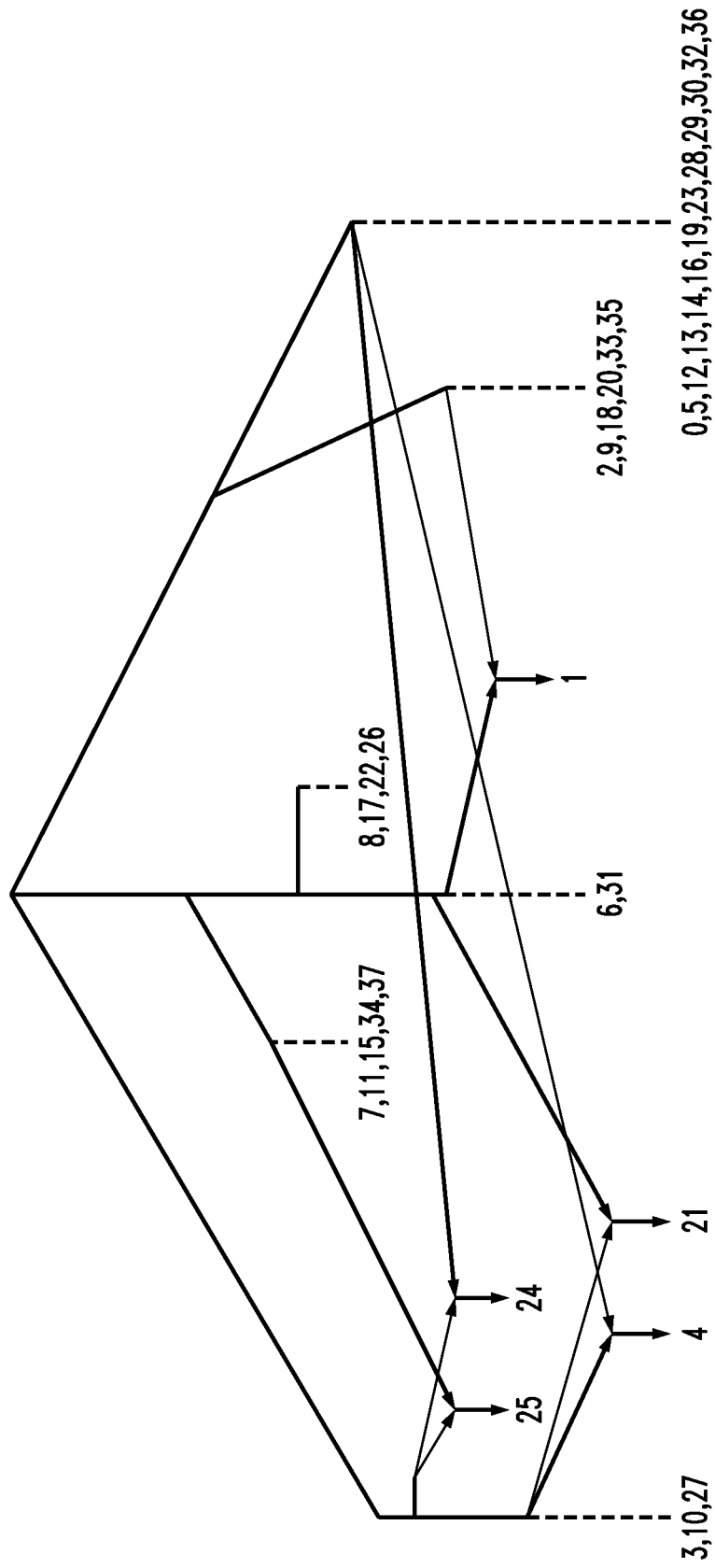

METHOD FOR RECONSTRUCTING EVOLUTIONARY DATA

FIELD OF THE INVENTION

The present invention generally relates to genetics, and, more particularly, to phylogeography.

BACKGROUND OF THE INVENTION

Anthropological and phylogeographical questions exist as to the origins of various species of beings. Each being carries ancestral material (such as, for example, single nucleotide polymorphisms (SNPs), short tandem repeat (STR) numbers, inversions, etc.) marked by signatures due to imperfections in deoxyribonucleic acid (DNA) replication. Such material tells a story about only a small fraction of the populations that have inhabited the planet (sometimes referred to as the surviving lineages).

One exemplary challenge exists in the form of the ancestor-derivative conundrum, wherein normally the ancestor cannot be distinguished from the derivative, and vice-versa, because, by definition, the two look alike.

Given the collection of mutations (for example, SNPs) in recombining DNA (for example, autosomal chromosomes) of the population of a species, a problem exists in the ability to infer units of recombination (that is, the process by which a strand of DNA is broken and then joined to the end of a different DNA molecule) and the recombination history of each individual. Applied to a population, the problem is, in essence, the ability to infer the ancient recombination graph of the population. The problem is particularly challenging due to recombination.

Existing approaches include combinatorics and statistics such as use counts, log lengths and frequencies. The existing approaches, however, produce signals that are unclear, and do not produce consistent rules obvious for false positives and false negatives.

Existing approaches also include a simple four-gamete rule. Such an approach, however, operates in the absence of recombinations and produces a significant amount of false positives with no apparent rules for eliminating them. Also, existing approaches include linkage disequilibrium (LD) analysis. Such an approach, however, is inadequate for data that includes high linkage disequilibrium.

SUMMARY OF THE INVENTION

Principles of the present invention provide techniques for reconstructing evolutionary data (for example, a lineage of genetic information for an individual and/or population).

An exemplary method (which may be computer-implemented) for reconstructing evolutionary data of a set of genomic data, according to one aspect of the invention, can include steps of obtaining a set of genomic data, determining a chronological order of one or more mutations within the set of genomic data, determining a chronological order of one or more recombinations within the set of genomic data, determining a position of each recombination within the set of genomic data, and combining the chronological order of the one or more mutations, the chronological order of the one or more recombinations and the position of each recombination to reconstruct evolutionary data of the set of genomic data.

At least one embodiment of the invention can be implemented in the form of a computer product including a computer usable medium with computer usable program code for performing the method steps indicated. Furthermore, at least one embodiment of the invention can be implemented in the form of an apparatus including a memory and at least one processor that is coupled to the memory and operative to perform exemplary method steps.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 3 is a diagram illustrating a table of an exemplary input data set, according to an embodiment of the present invention;

FIG. 6 is a diagram illustrating a tree relating to chromosome 21 data, according to an embodiment of the present invention;

FIG. 7 is a diagram illustrating a tree relating to chromosome 21 data, according to an embodiment of the present invention;

FIG. 8 is a diagram illustrating a tree relating to chromosome 21 data, according to an embodiment of the present invention;

FIG. 9 is a diagram illustrating a tree relating to chromosome 21 data, according to an embodiment of the present invention.

DETAILED DESCRIPTION OF PREFERRED EMBODIMENTS

Figure 1:
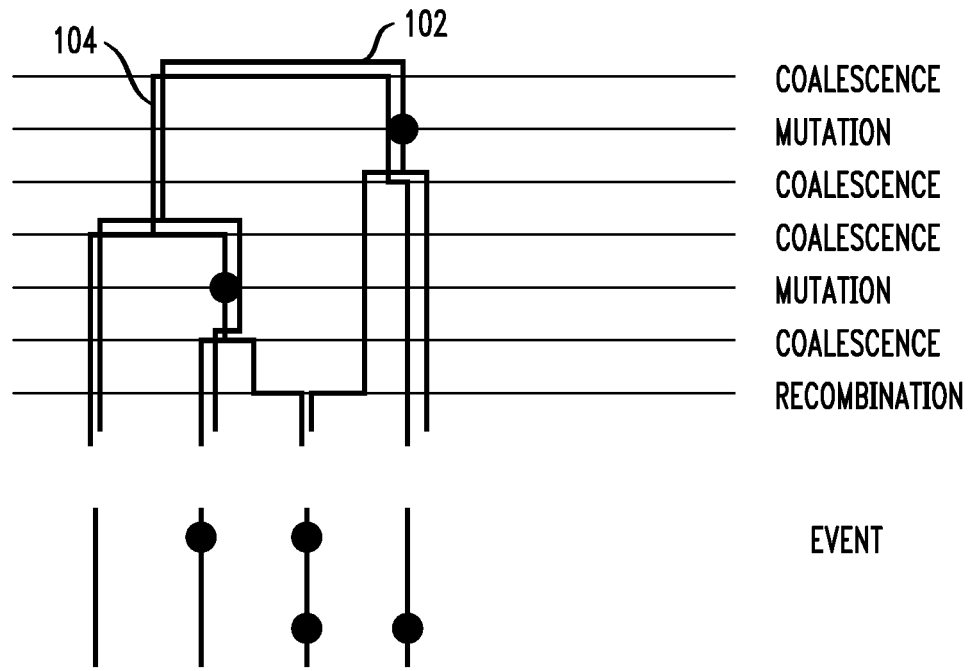
FIG. 1 is a diagram illustrating a combined history of coalescence and recombination, according to an embodiment of the present invention.

Principles of the present invention include providing a parsimonious ancient recombination graph (also referred to herein as a compatibility graph) incorporating the use of recombining DNA sequences. Using exclusively non-recombining DNA sequences produces only partial evolutionary data, as they represent only a small part of the genome, behave as a single locus and include uni-linear (exclusively male or female) transmission. By incorporating recombining DNA sequences and examining across multiple SNPs, a determination can be made as to the relationship between the SNPs.

Using recombination events as phylogenetic markers can, for example, facilitate the use of any autosome, recognize recombination events between differentiated lineages, and enable one to use recombinations in the same way as mutations (or Y-str markers (Y-str markers are short tandem repeats found on the Y chromosome)).

One or more embodiments of the invention can be useful for phylogenetic purposes, wherein the relatedness of various sets of genetic data can be determined. For example, the techniques described herein can be used to determine commonalties between virus samples, thereby facilitating therapeutic benefits.

Additionally, one or more embodiments of the present invention can be useful for phylogeographic purposes, wherein the history of the migration of a population (for example, which population moved to which geographic location(s) and mixed with which additional population(s)) can be determined.

Principles of the present invention also distinguish recombinant patterns from non-recombinant patterns, and identify ancient recombinations. Distinguishing recombinant patterns from non-recombinant patterns cannot be accomplished simply by looking at patterns, but rather is performed by using a tree. Additionally, principles of the invention include mathematic feasibility including a heuristic-free combinatorial algorithm as well as statistical possibilities that incorporate heuristics.

One or more embodiments of the present invention include a compatibility model (also referred to herein as a parsimony model). Given a set of data (for example, genomic data), a compatibility model can produce a tree (that is, a graph) with a minimum cost that explains die set of data. Cost, as used herein, is the number of mutations and the number of recombinations that are required to explain the data. As an example, each change on the tree (graph) can contribute one to the cost. Each edge of the tree (graph) is annotated with a SNP value. A mutation is the SNP value.

Within a set of data, patterns of length L are examined to construct (for example, via a combinatorial algorithm) a compatibility graph that includes sequences of L-sized patterns in order to illustrate the phylogeny of the data.

Using a known theorem such as, for example, $$X = \sum_c (a_c - 1),$$

(wherein c represents the number of columns and $a_c$ represents the number of distinct values per column) given a data set D, the cost of a tree on D cannot fall below X. If there are no homoplasies (or recurrent mutations), the cost of the most parsimonious tree is exactly X and this (un-rooted) tree is unique.

In one or more embodiments of the invention, using an ancient recombination graph (ARG) theorem such as, for example, given a data set D, the cost of the ARG on D cannot fall below X+R (wherein R is the number of recombinations). Also, if there are no homoplasies (or recurrent mutations), the cost of the most parsimonious ARG is exactly X+R and this ARG is unique (except for some linear positional variations). As such, minimizing the mutation-cost is sufficient, as it implies minimization of the number of recombinations.

Using an algorithm, given a data set D, the most parsimonious tree is not necessarily unique. Additionally, the challenge of discovering this tree is NP-hard. It follows, as such, that given a data set D, the most parsimonious ARG is not necessarily unique, and the challenge of discovering this ARG is NP-hard.

As described herein, one or more embodiments of the invention include a compatibility model that chronologically orders the (coalescent) mutations and recombinations of a set of data (that is, a set of genomic data).

FIG. 1 is a diagram illustrating a combined history of coalescence and recombination, according to an embodiment of the present invention. By way of illustration, FIG. 1 depicts a pair of graphs, 102 and 104 that individually are trees, that is, contain no cycles. As illustrated in FIG. 1, however, when combined, the combined graph is no longer a tree (that is, it contains cycles).

For purposes of illustration, assume the circle on element 104 is red, and the circle on element 102 is blue. If we are given three samples, a first with one red, a second with one red and one blue, and a third with one blue, then it is most likely that there were at least two ancestors: one with one red, the other with one blue, and that the second was a recombination between these two. The probability that the one red and one blue evolved independently or from either of the red or blue ancestor is very low.

Figure 2:
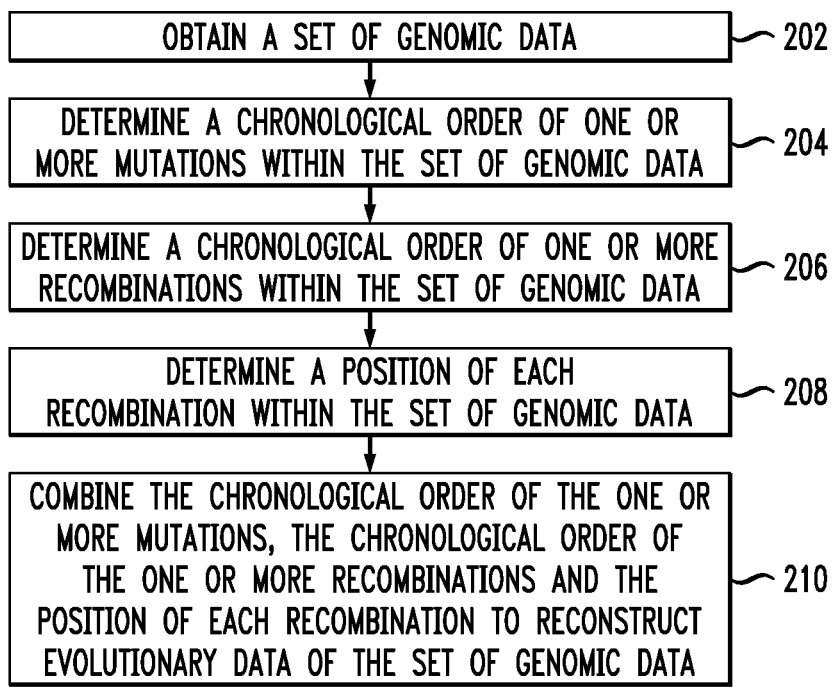
FIG. 2 is a flow diagram illustrating techniques for reconstructing evolutionary data of a set of genomic data, according to an embodiment of the present invention.

FIG. 2 is a flow diagram illustrating techniques for reconstructing evolutionary data of a set of genomic data, according to an embodiment of the present invention. Step 202 includes obtaining a set of genomic data. The set of genomic data can include a sequence of one or more patterns, wherein the sequence is a pre-determined length. Step 204 includes determining a chronological order of one or more mutations within the set of genomic data. As described herein, determining a chronological order of the one or more mutations and one or more recombinations can include using a heuristic-free combinatorial algorithm. The chronological order is preferably obtained by reversing down the tree or graph. The earlier events are towards the root (that is, the top end of the figures) and the later events are towards the leaves of the tree (that is, the bottom end in the figures).

Step 206 includes determining a chronological order of one or more recombinations within the set of genomic data. Determining a chronological order of one or more recombinations can include distinguishing one or more recombinant patterns from one or more non-recombinant patterns via examining the graph or tree.

Step 208 includes determining a position of each recombination within the set of genomic data. Determining the position of each recombination can be performed by examining the constructed graph or tree. The steps of determining a chronological order of one or more mutations, determining a chronological order of one or more recombinations and determining a position of each recombination within the set of genomic data can be performed simultaneously.

Step 210 includes combining the chronological order of the one or more mutations, the chronological order of the one or more recombinations and the position of each recombination to reconstruct evolutionary data of the set of genomic data. The reconstructed evolutionary data may include a topology. A topology is the ordering of the mutations and the recombinations in the genomic data set. The reconstructed evolutionary data may also enumerate the one or more recombinations, wherein the recombinations may include at least one of one or more ancient recombinations and one or more recent recombinations. Also, reconstructed evolutionary data may identify one or more participating lineages.

One or more embodiments of the present invention may also include the additional step of generating one or more multifurcating trees that encode the one or more mutations and the one or more recombinations.

As explained herein, an illustrative embodiment of the present invention includes obtaining an input sample (for example, sample haplotypes), using the input to create SNP blocks and using the SNP blocks to infer topology (for example, ARG).

The structure of a topology G can include the following elements. Each leaf node has exactly one incident edge, and each edge is assigned a direction (wherein different root nodes (no incoming edge) are possible). Labeled nodes can include leaf nodes labeled by some set of given samples (for example, rows) and non-leaf nodes with exactly one incoming edge (wherein the label (feature f) goes with the incoming edge). Also, the union of all the labels of reachable leaf nodes can be represented as g(f).

Topology G is compatible with D if there is a unique edge in G with a label f of each column, and S(f)=g(f), for each f. S(f) is the collection of samples in input D that have the label f in the appropriate column. An ancestral recombination graph (ARG) is a compatible graph defined on k segments G(k), wherein a node can have at most two incoming edges (that is, two parents). Also, two parents can denote recombination of two segments, and an incoming edge can be labeled by one segment each. Each segment corresponds to that part of the input that can have a non-recombining history.

Topology G is compatible with D if the condition of S(f)=g(f), for each f is disregarded for at most one f per column. As such, the ancestral state of column two is c. The state that is missing in the graph, or the state in which the column was at the very beginning, is to be interpreted as the ancestral state. Also, when features take binary values (that is, it takes only two values (not more)), it is also referred to as the four-gamete rule.

Recall that in one or more embodiments of the invention, a tree can include exactly one path between any two nodes, and a tree can be an ARG with k=1 segment.

A path on an ARG can be specific to a segment 1, and no edge can be labeled by a segment 1'. Also, between any two nodes on ARG G, there can exist at most k paths. Nodes are incomparable in ARG G(k) when G is defined over k segments. Recall that in one or more embodiments of the invention, a tree can include two nodes that do not lie on a path from root to leaf node for all leaf nodes. Additionally, one or more embodiments of the invention can include an ARG wherein two nodes do not lie on all of k paths from root to leaf node for all leaf nodes. As such, two nodes that are incomparable must lie on two different paths on the ARG.

Properties of a compatible G (ARG) can include, for example, the following. An incomparable property includes nodes corresponding to each feature per column that are incomparable in G. An optimization problem includes when nodes have multiple parents. In such an instance, G may not be unique, and some optimality constraint has to be introduced.

As described herein, a consensus ARG can include the following elements. Each column can be viewed as a star graph (that is, tree). Given two graphs, one can build a consensus ARG. Instead of a single column star tree, a tree over multiple columns can be used. As a result, an algorithm to build a consensus ARG given two graphs is adequate.

An invariance condition can include an incomparable theorem as follows. If node labels in G1 (f1) and G2 (f2) are incomparable, and labels of G, with g(f1 and f2)=S(f1)+S(f) where the label of G1, or the label of G2, or the label of G1 and G2, then the labels of G are incomparable.

One or more embodiments of the present invention include a consensus algorithm referred to herein as the dominant, subdominant, recombinant (DSR) algorithm. The DSR algorithm includes an edge-label driven algorithm and is based on the incomparable theorem. A DSR Algorithm can include an input of two graphs (for example, G1 and G2) and an output of a consensus ARG G.

In an illustrative embodiment, a DSR algorithm can include the following elements. G1 and G2 can be defined on leaf labels L. Universe U is assigned the set L. P1 and P2 can be partitions on U at leaf level. "DO-WHILE" marks the beginning of the loop described in this paragraph (see the last sentence of this paragraph for the conclusion of the loop). Also, a DSR algorithm can include a network structure with nodes in G and the labels derived from P1 and P2. Universe U is assigned the nodes in G. A layer can be incremented, and P1 and P2 can be updated as sets on U of this layer, wherein P1 can have labels from G1 and P2 can have labels from G2. "WHILE" includes wherein P1 is non-empty or P2 is non-empty. The statements between "DO-WHILE" and "WHILE" are repeated as long as P1 is non-empty and P2 is non-empty.

In one or more embodiments of the invention, a DSR algorithm can also include the following elements. Given two partitions, P1 and P2, of some universe U, p can be a maximal intersection of p1 in P1 and p2 in P2. Also, each p1 and each p2 can be labeled. In such an example, the dominant component includes p having labels of p1 and p2, the subdominant component includes p having a label of p1 or p2, and the recombinant component includes p having no labels (that is, neither p1 nor p2).

DSR assignment rules can be constrained by topology. Each entry in x-matrix is a node in consensus ARG G. An x-matrix is the intersection matrix. Each entry in the intersection matrix is assigned as dominant or subdominant or recombinant, respecting the rules stated herein. DSR assignment rules state that each row and each column has at most one dominant. If a row or a column does not have a dominant, it can have at most one subdominant. The remaining rows and/or columns are designated as recombinants. Also, in one or more embodiments of the invention, a non-recombinant can have non-recombinants either in its row or its column, but not in both.

Topology (that is, structure) construction can include the following elements. The elements in x-matrix are nodes in a consensus ARG G. The DSR assignment guarantees a feasible topology at the current layer. Also, the roles of DSR carried to next layer to maintain continuity of feasible topology.

In one or more embodiments of the invention, determining where the recombinations in a final graph (for example, ARG G) come from includes referring to the assignments of the entries in an intersection matrix (as described above). Recall that recombinants can be assigned within each layer and subdominants across layers. If the dominants are matched, they are elements in the x-matrix. If the dominants are not matched, they do not belong to the x-matrix.

In one or more embodiments of the present invention, the correctness of a DSR algorithm includes elements of being based on an incomparable theorem, as well as whenever there are two parents, ensuring that the two are from different segments (for example, within a layer and/or across layers (matching designated nodes)).

Accordingly, FIG. 3 through FIG. 5B illustrate an exemplary input and output in connection with the principles described above.

FIG. 3 is a diagram illustrating a table 302 of an exemplary input data set, according to an embodiment of the present invention. By way of illustration, FIG. 3 depicts a data set wherein each column represents a SNP value. The reference sequence can be, for example, an arbitrary sequence.

The exemplary input data set illustrated in FIG. 3 is derived from Wright-Fisher, and contains a constant population (150) model. The sequence length of the data set is 156,589 base pairs, the mutation rate is 0.000006118 positions per generation (pos/generation) and the recombination rate is 0.018 centiMorgans per Megabase (cM/Mb). This results in the data set including 215 polymorphic sites (SNPS), 150 samples (including 60 haplotypes), and 40,000 generations.

As illustrated in FIG. 3, the samples are separated into groups, wherein each group includes one or more columns from the sample data (wherein "C" stands for columns). Group 0 includes C1, C10, C80, C4, C85, C20, C32, C86 and C110. Group 1 includes C100, C121, C7, C51, C12, C39 and C117. Group 2 includes C11, C48, C137, C27, C108 and C50. Group 3 includes C52, C9, C53, C5, C45, C123 and C103. Group 4 includes C38, C107, C114, C54, C140 and C115. Group 5 includes C6, C3, C120 and C93. Group 6 includes C33, C2 and C92. Group 7 includes C74, C34, C29 and C150. Group 8 includes C40 and C81. Group 9 includes C47, C16, C91 and C8. Group 10 includes C143. Group 11 includes C21. Group 12 includes C36. Group 13 includes C19. Group 14 includes C24. Group 15 includes C148. Group 16 includes C118.

Figure 4:
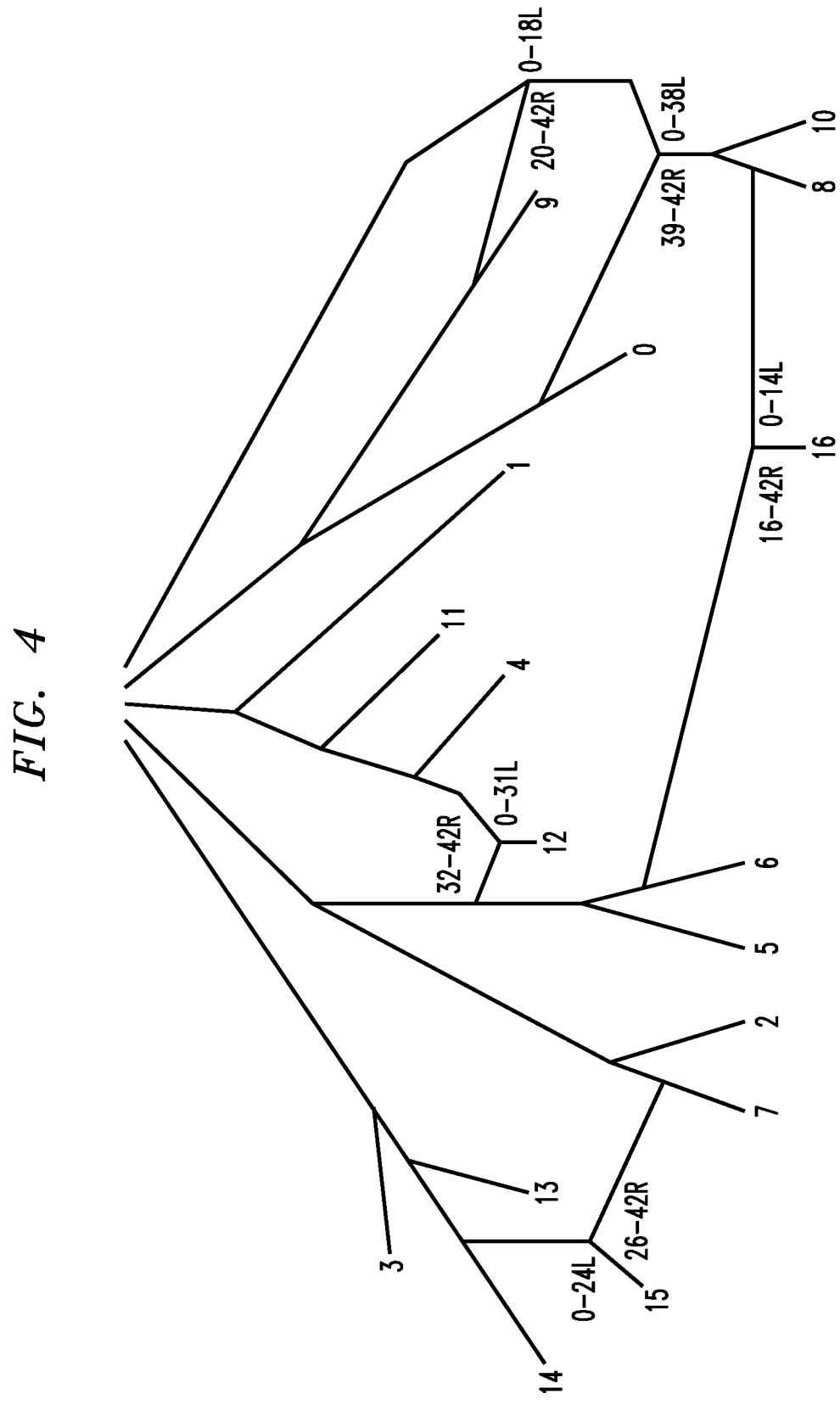
FIG. 4 is a diagram illustrating a tree relating to the exemplary input data set of FIG. 3, according to an embodiment of the present invention.

FIG. 4 is a diagram illustrating a tree relating to the exemplary input data set of FIG. 3, according to an embodiment of the present invention. As depicted in FIG. 4, the recombinant groups are Group 15 (including C148), Group 12 (including C36) and Group 16 (including C118). Also, Group 8 (including C40 and C81) and Group 10 (including C143) include ancient recombinations as depicted in FIG. 4. For example, the two ancestors of Group 16 are a common ancestor of Groups 5 and 6, and a common ancestor of Groups 8 and 10.

Also, by way of illustration, FIG. 4 depicts branches of the tree that are labelled with the corresponding Group numbers detailed above. For instance, FIG. 4 depicts Groups 3, 14, 13, 15, 7, 2, 5, 6, 12, 4, 11, 1, 16, 0, 9, 8 and 10. Additional numbers are depicted in FIG. 4 that are used to identify and describe recombinations. For example, 0-24L, 26-42R indicates that the data has SNP positions from 0 to 42, and the recombination occurs at position 24 (that is, the left and right of this position have different ancestry).

Figure 5A:
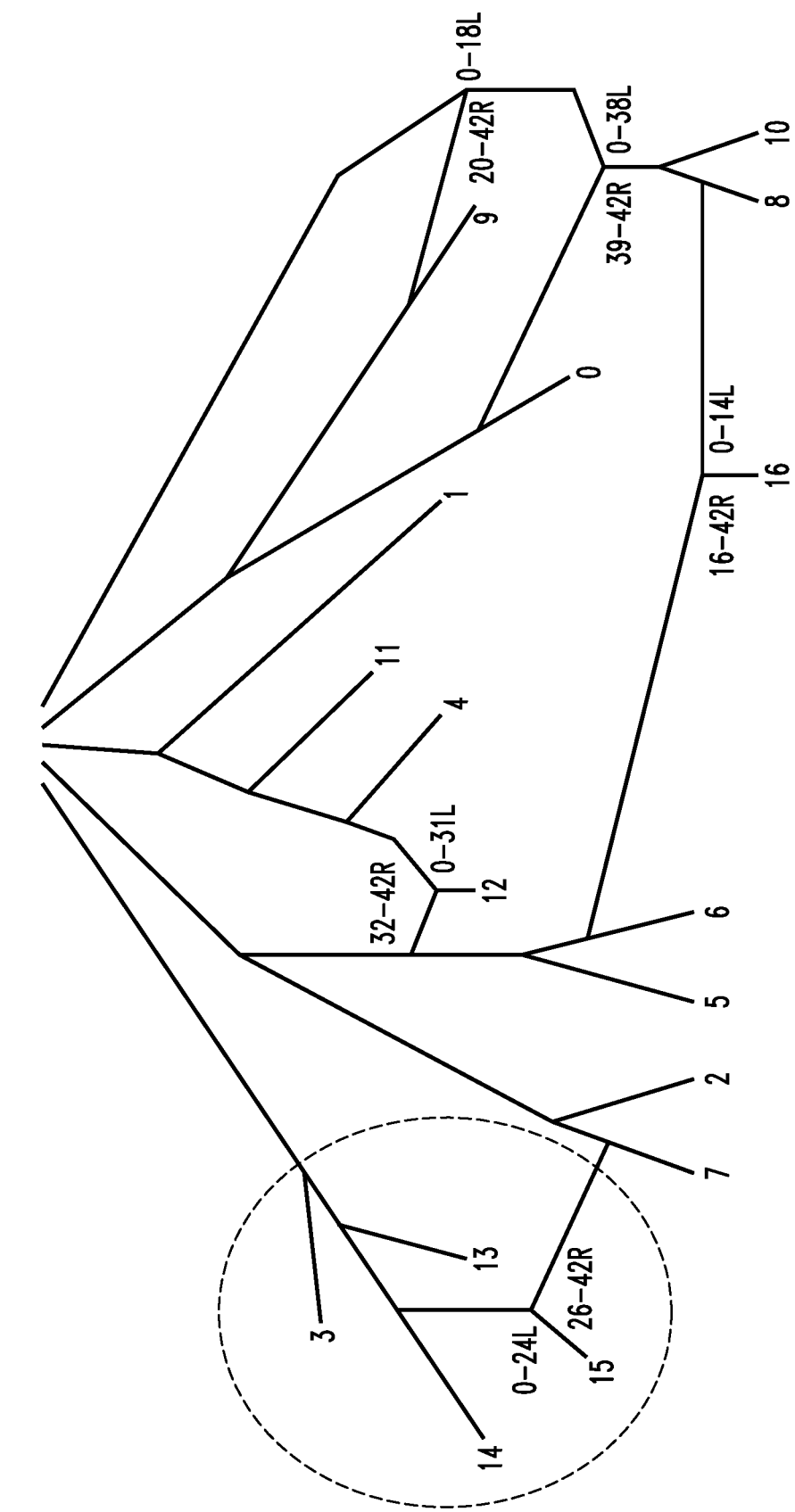
FIG. 5A is a diagram illustrating a tree relating to the exemplary input data set of FIG. 3, according to an embodiment of the present invention.

FIG. 5A is a diagram illustrating a tree (that is, the same tree depicted in FIG. 4) relating to the exemplary input data set of FIG. 3, according to an embodiment of the present invention. FIG. 5A also includes a circled region that is examined more closely in FIG. 5B.

Figure 5B:
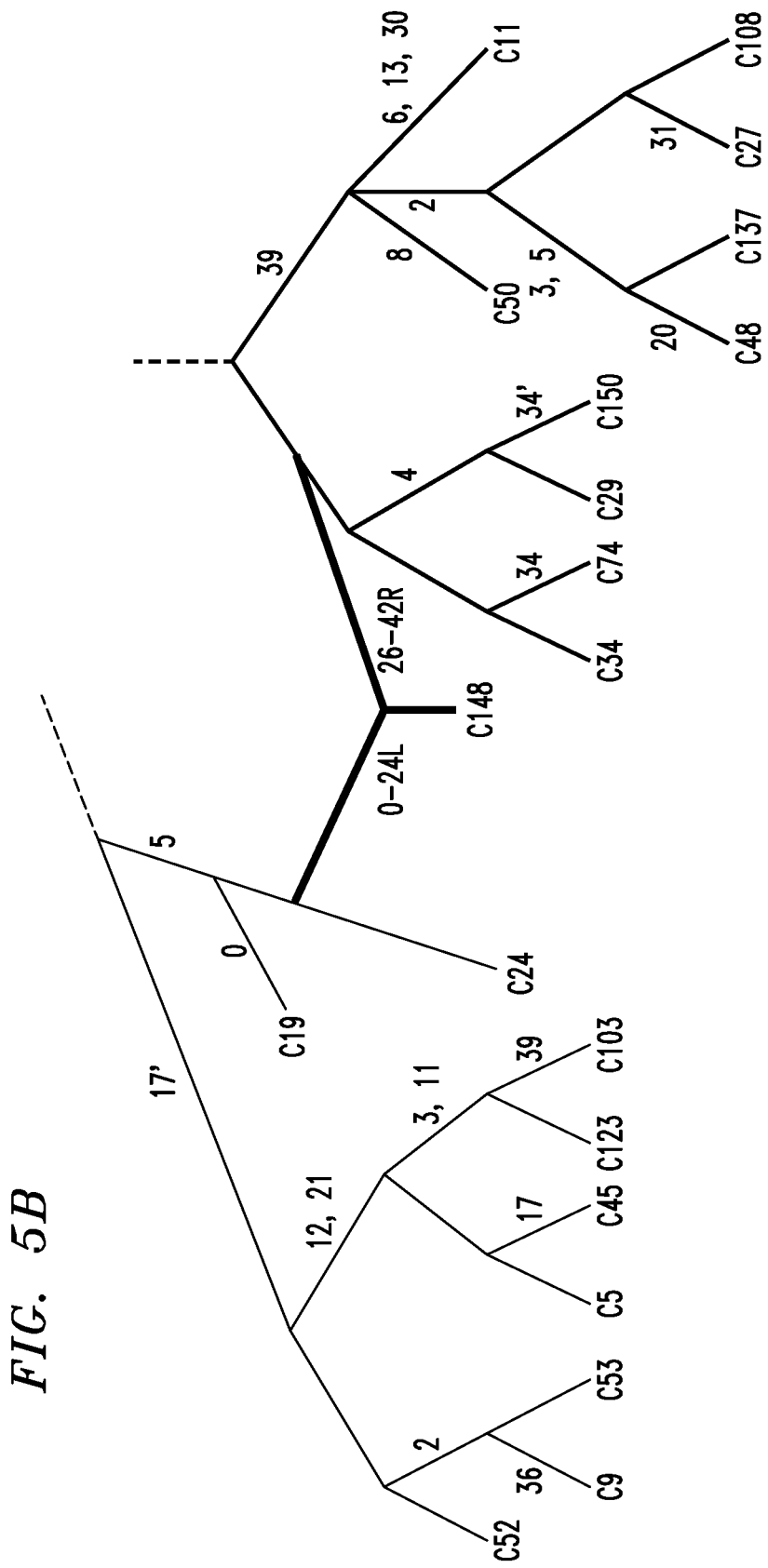
FIG. 5B is a diagram illustrating a tree relating to the exemplary input data set of FIG. 3, according to an embodiment of the present invention.

FIG. 5B is a diagram illustrating a tree relating to the exemplary input data set of FIG. 3, according to an embodiment of the present invention. Additionally, FIG. 4 provides a skeleton of the graph and FIG. 5B provides further details. By way of illustration, FIG. 5B depicts a closer examination of the circled region of the tree depicted in FIG. 5A. The sample numbers (that is, C52, C9, C53, C45, C123, C103, C19, C24, C148, C34, C74, C29, C150, C50, C11, C48, C137, C27 and C108) correspond to samples depicted in FIG. 3. The additional numbers depicted in FIG. 5B (for example, 36, 2, 17, etc.) are SNP position in the data.

FIG. 6 through FIG. 9 includes chromosome 21 (recombining) data that contains Chinese (two sub-populations) and Japanese data of approximately 200 SNPs. FIG. 6 is a diagram illustrating a tree relating to chromosome 21 data, according to an embodiment of the present invention. By way of illustration, FIG. 6 depicts SNP positions 10-69. In FIG. 6 through FIG. 9, the numbers are the leaf-nodes are group numbers. The SNP positions from 10-69 are represented by one tree from position 10 to 44 and another tree from position 50 to 69, as well as the consensus of the two trees illustrating the recombinants. The recombinants include the descendants of the pairs of meeting arrows. Also, in FIG. 6 through FIG. 9, some positions are not illustrated because they belong to extremely high variablility regions.

FIG. 7 is a diagram illustrating a tree relating to chromosome 21 data, according to an embodiment of the present invention. By way of illustration, FIG. 7 depicts SNP positions 50-89. The SNP positions from 50-89 are represented by one tree from position 50 to 69 and another tree from position 75 to 89, as well as the consensus of the two trees illustrating the recombinants. The recombinants include the descendants of the pairs of meeting arrows.

FIG. 8 is a diagram illustrating a tree relating to chromosome 21 data, according to an embodiment of the present invention. By way of illustration, FIG. 8 depicts SNP positions 75-114. The SNP positions from 75-114 are represented by one tree from position 75 to 84 and another tree from position 105 to 114, as well as the consensus of the two trees illustrating the recombinants. The recombinants include the descendants of the pairs of meeting arrows.

FIG. 9 is a diagram illustrating a tree relating to chromosome 21 data, according to an embodiment of the present invention. By way of illustration, FIG. 9 depicts SNP positions 105-129. The SNP positions from 105-129 are represented by one tree from position 105 to 114 and another tree from position 115 to 129, as well as the consensus of the two trees illustrating the recombinants. The recombinants include the descendants of the pairs of meeting arrows.

A variety of techniques, utilizing dedicated hardware, general purpose processors, software, or a combination of the foregoing may be employed to implement the present invention. At least one embodiment of the invention can be implemented in the form of a computer product including a computer usable medium with computer usable program code for performing the method steps indicated. Furthermore, at least one embodiment of the invention can be implemented in the form of an apparatus including a memory and at least one processor that is coupled to the memory and operative to perform exemplary method steps.

Figure 10:
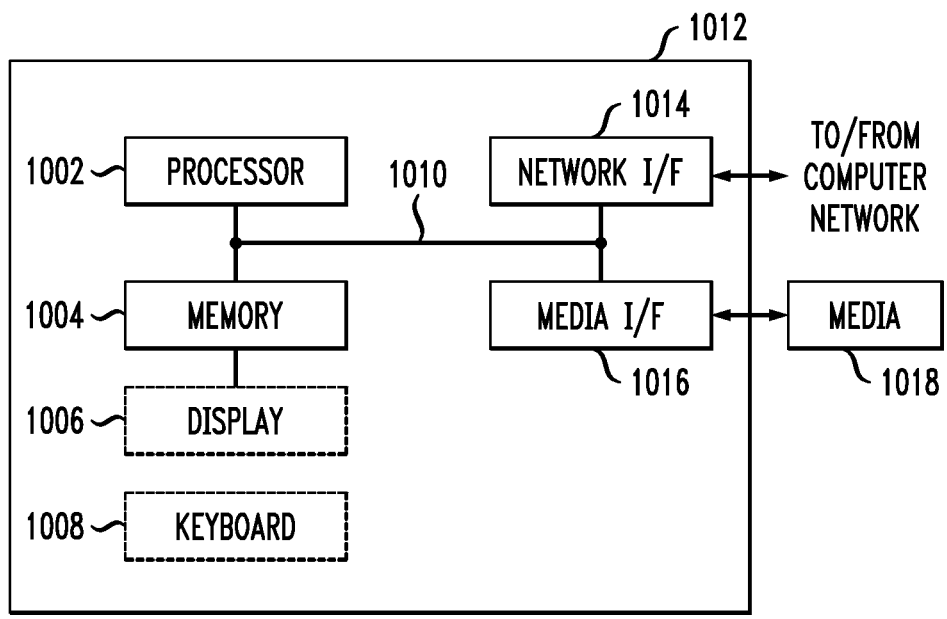
FIG. 10 is a system diagram of an exemplary computer system on which at least one embodiment of the present invention can be implemented.

At present, it is believed that the preferred implementation will make substantial use of software running on a general-purpose computer or workstation. With reference to FIG. 10, such an implementation might employ, for example, a processor 1002, a memory 1004, and an input and/or output interface formed, for example, by a display 1006 and a keyboard 1008. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input and/or output interface" as used herein, is intended to include, for example, one or more mechanisms for inputting data to the processing unit (for example, mouse), and one or more mechanisms for providing results associated with the processing unit (for example, printer). The processor 1002, memory 1004, and input and/or output interface such as display 1006 and keyboard 1008 can be interconnected, for example, via bus 1010 as part of a data processing unit 1012. Suitable interconnections, for example via bus 1010, can also be provided to a network interface 1014, such as a network card, which can be provided to interface with a computer network, and to a media interface 1016, such as a diskette or CD-ROM drive, which can be provided to interface with media 1018.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and executed by a CPU. Such software could include, but is not limited to, firmware, resident software, microcode, and the like.

Furthermore, the invention can take the form of a computer program product accessible from a computer-usable or computer-readable medium (for example, media 1018) providing program code for use by or in connection with a computer or any instruction execution system. For the purposes of this description, a computer usable or computer readable medium can be any apparatus for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory (for example, memory 1004), magnetic tape, a removable computer diskette (for example, media 1018), a random access memory (RAM), a read-only memory (ROM), a rigid magnetic disk and an optical disk. Current examples of optical disks include compact disk-read only memory (CD-ROM), compact disk-read and/or write (CD-R/W) and DVD.

A data processing system suitable for storing and/or executing program code will include at least one processor 1002 coupled directly or indirectly to memory elements 1004 through a system bus 1010. The memory elements can include local memory employed during actual execution of the program code, bulk storage, and cache memories which provide temporary storage of at least some program code in order to reduce the number of times code must be retrieved from bulk storage during execution.

Input and/or output or I/O devices (including but not limited to keyboards 1008, displays 1006, pointing devices, and the like) can be coupled to the system either directly (such as via bus 1010) or through intervening I/O controllers (omitted for clarity).

Network adapters such as network interface 1014 may also be coupled to the system to enable the data processing system to become coupled to other data processing systems or remote printers or storage devices through intervening private or public networks. Modems, cable modem and Ethernet cards are just a few of the currently available types of network adapters.

In any case, it should be understood that the components illustrated herein may be implemented in various forms of hardware, software, or combinations thereof, for example, application specific integrated circuit(s) (ASICS), functional circuitry, one or more appropriately programmed general purpose digital computers with associated memory, and the like. Given the teachings of the invention provided herein, one of ordinary skill in the related art will be able to contemplate other implementations of the components of the invention.

At least one embodiment of the invention may provide one or more beneficial effects, such as, for example, incorporating recombining DNA sequences in evolutionary data.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A computer-implemented method for reconstructing evolutionary data of a set of haplotype data, comprising the steps of:

providing a system, wherein the system comprises distinct software components, each of the distinct software components being embodied on a tangible computer-readable recordable storage medium;

obtaining two or more sets of haplotype data, wherein each set of haplotype data comprises a graph, and wherein obtaining two or more sets of haplotype data is carried out by a software component executing on a hardware processor;

determining a chronological order of one or more mutations within the two or more sets of haplotype data by applying a heuristic-free combinatorial algorithm to each set of haplotype data, wherein determining a chronological order of one or more mutations is carried out by a software component executing on a hardware processor;

determining a chronological order of one or more recombinations within the two or more sets of haplotype data by applying a heuristic-free combinatorial algorithm to each set of haplotype data, wherein determining a chronological order of one or more recombinations is carried out by a software component executing on a hardware processor;

determining a position of each recombination within the two or more sets of haplotype data, wherein determining a position of each recombination is carried out by a software component executing on a hardware processor; and combining the chronological order of the one or more mutations, the chronological order of the one or more recombinations and the position of each recombination to reconstruct evolutionary data of the two or more sets of haplotype data to determine relatedness of the two or more sets of haplotype data via generating a consensus graph via a consensus algorithm to infer topology of the haplotype data, wherein the consensus graph is generated from the two or more graphs of haplotype data, and wherein topology of the haplotype data comprises an ordering the one or more mutations and the one or more recombinations in the haplotype data, wherein combining the chronological order of the one or more mutations, the chronological order of the one or more recombinations and the position of each recombination to reconstruct evolutionary data of the two or more sets of haplotype data is carried out by a software component executing on a hardware processor.

2. The method of claim 1, wherein the step of determining a chronological order of one or more recombinations comprises distinguishing one or more recombinant patterns from one or more non-recombinant patterns.

3. The method of claim 1, wherein each set of haplotype data comprises a sequence of one or more patterns, wherein the sequence is a pre-determined length.

4. The method of claim 1, wherein the steps of determining a chronological order of one or more mutations, determining a chronological order of one or more recombinations and determining a position of each recombination within the two or more sets of haplotype data are performed simultaneously.

5. The method of claim 1, further comprising the additional step of generating one or more multifurcating trees that encode the one or more mutations and the one or more recombinations.

6. The method of claim 1, wherein the reconstructed evolutionary data enumerates the one or more recombinations.

7. The method of claim 6, wherein the one or more recombinations comprise at least one of one or more recombinations from one or more generations.

8. The method of claim 1, wherein the reconstructed evolutionary data identifies one or more participating lineages.

9. A computer program product comprising a tangible computer readable storage medium having computer readable program code for reconstructing evolutionary data of a set of haplotype data, said computer program product including:
- computer readable program code for obtaining two or more sets of haplotype data, wherein each set of haplotype data comprises a graph;
- computer readable program code for determining a chronological order of one or more mutations within the two or more sets of haplotype data by applying a heuristic-free combinatorial algorithm to each set of haplotype data;
- computer readable program code for determining a chronological order of one or more recombinations within the two or more sets of haplotype data by applying a heuristic-free combinatorial algorithm to each set of haplotype data;
- computer readable program code for determining a position of each recombination within the two or more sets of haplotype data; and
- computer readable program code for combining the chronological order of the one or more mutations, the chronological order of the one or more recombinations and the position of each recombination to reconstruct evolutionary data of the two or more sets of haplotype data to determine relatedness of the two or more sets of haplotype data via generating a consensus graph via a consensus algorithm to infer topology of the haplotype data, wherein the consensus graph is generated from the two or more graphs of haplotype data, and wherein topology of the haplotype data comprises an ordering the one or more mutations and the one or more recombinations in the haplotype data.

10. The computer program product of claim 9, wherein the computer readable program code for determining a chronological order of one or more recombinations comprises computer readable program code for distinguishing one or more recombinant patterns from one or more non-recombinant patterns.

11. The computer program product of claim 9, further comprising computer readable program code for generating one or more multifurcating trees that encode the one or more mutations and the one or more recombinations.

12. The computer program product of claim 9, wherein the computer readable code for combining the chronological order of the one or more mutations, the chronological order of the one or more recombinations and the position of each recombination to reconstruct evolutionary data of the two or more sets of haplotype data comprises at least one of:
- computer readable program code for enumerating the one or more recombinations; and
- computer readable program code for identifying one or more participating lineages.

13. An apparatus for reconstructing evolutionary data of a set of haplotype data, comprising:
- a memory; and
- at least one processor coupled to said memory and operative to:
  - obtain two or more sets of haplotype data, wherein each set of haplotype data comprises a graph;
  - determine a chronological order of one or more mutations within the two or more sets of haplotype data by applying a heuristic-free combinatorial algorithm to each set of haplotype data;
  - determine a chronological order of one or more recombinations within the two or more sets of haplotype data by applying a heuristic-free combinatorial algorithm to each set of haplotype data;
  - determine a position of each recombination within the two or more sets of haplotype data; and
  - combine the chronological order of the one or more mutations, the chronological order of the one or more recombinations and the position of each recombination to reconstruct evolutionary data of the two or more sets of haplotype data to determine relatedness of the two or more sets of haplotype data via generating a consensus graph via a consensus algorithm to infer topology of the haplotype data, wherein the consensus graph is generated from the two or more graphs of haplotype data, and wherein topology of the haplotype data comprises an ordering the one or more mutations and the one or more recombinations in the haplotype data.

14. The apparatus of claim 13, wherein the at least one processor coupled to said memory and operative to determine a chronological order of one or more recombinations is further operative to distinguish one or more recombinant patterns from one or more non-recombinant patterns.

15. The apparatus of claim 13, wherein the at least one processor coupled to said memory is further operative to:
- generate one or more multifurcating trees that encode the one or more mutations and the one or more recombinations.

16. The apparatus of claim 13, wherein in combining the chronological order of the one or more mutations, the chronological order of the one or more recombinations and the position of each recombination to reconstruct evolutionary data of the two or more sets of haplotype data, the at least one processor coupled to said memory is further operative to perform at least one of:
- enumerating the one or more recombinations; and
- identifying one or more participating lineages.

* * * * *